US008999407B2

(12) United States Patent
Salomon et al.

(10) Patent No.: US 8,999,407 B2
(45) Date of Patent: Apr. 7, 2015

(54) NATURAL INSECT REPELLENT COMPOSITIONS

(76) Inventors: Steven Fred Salomon, Daniel Island, SC (US); Gail Anne Salomon, Daniel Island, SC (US)

( * ) Notice: Subject to any disclaimer, the term of this patent is extended or adjusted under 35 U.S.C. 154(b) by 138 days.

(21) Appl. No.: 13/200,767

(22) Filed: Sep. 30, 2011

(65) Prior Publication Data
US 2013/0084347 A1 Apr. 4, 2013

(51) Int. Cl.
*A01N 65/28* (2009.01)
*A01N 65/00* (2009.01)
*A01N 65/08* (2009.01)
*A01N 65/24* (2009.01)
*A01N 65/44* (2009.01)

(52) U.S. Cl.
CPC ............... *A01N 65/28* (2013.01); *A01N 65/00* (2013.01); *A01N 65/08* (2013.01); *A01N 65/24* (2013.01); *A01N 65/44* (2013.01)

(58) Field of Classification Search
CPC ..................................................... A61K 36/61
See application file for complete search history.

(56) References Cited

U.S. PATENT DOCUMENTS

| | | | |
|---|---|---|---|
| 5,965,137 | A | 10/1999 | Petrus |
| 6,300,324 | B1 | 10/2001 | Partelow |
| 7,201,926 | B2 | 4/2007 | Fried et al. |
| 7,846,464 | B2 | 12/2010 | Darling |
| 2002/0034556 | A1 | 3/2002 | Khazan |
| 2005/0112164 | A1 | 5/2005 | Lewey |
| 2006/0057174 | A1 | 3/2006 | Meyhoefer |
| 2006/0182775 | A1 | 8/2006 | Everett |
| 2007/0166342 | A1 | 7/2007 | Darling |
| 2009/0169656 | A1 | 7/2009 | Porter et al. |
| 2010/0196520 | A1 | 8/2010 | Elraz |
| 2010/0197786 | A1 | 8/2010 | Elraz |
| 2010/0323939 | A1 | 12/2010 | Eng |
| 2011/0123655 | A1 | 5/2011 | Robinson |

FOREIGN PATENT DOCUMENTS

| | | | |
|---|---|---|---|
| CN | 101233864 A | * | 8/2008 |
| JP | 2001163716 A | * | 6/2001 |

OTHER PUBLICATIONS eHow Health Editor. "How to Use Geranium Oil as an Insect Repellent". Internet Archive Date: May 23, 2008. [Retrieved from the Internet on: Jan. 7, 2013]. Retrieved from the Internet: <URL: http://web.archive.org/web/20080523133812/http://www.ehow.com/how_2164044_use-geranium-oil-as-insect.html>.*
MacDowell, S. "All Natural Mosquito Repellent Recipe with Lemon Oil". Internet Archive Date: Jul. 1, 2010 [Retrieved from the Internet on: Jan. 7, 2013]. Retrieved from the Internet: <URL: http://web.archive.org/web/20100701144448/http://www.ehow.com/way_5179366_natural-repellent-recipe-lemon-oil.html>.*
Moore et al. J Med Entomol. Jul. 2007;44(4):624-630 (abstract only).*
Noosidum et al. J Vector Ecol. Dec. 2008;33(2):305-312 (abstract only).*
(U1) Experience Essential Oils.com. "Natural Mosquito Repellent Made Perfectly with Essential Oils". Internet Archive Date: Dec. 30, 2010. [Retrieved from the Internet on: Jan. 7, 2013]. Retrieved from the Internet: <URL: http://web.archive.org/web/20101230092625/http://www.experience-essential-oils.com/natural-mosquito-repellent.html>.*
(V1) Sanders, K. M. "Natural Repellets—A better choice to keep the bugs away". Jun. 2005 [Retrieved from the Internet on: Sep. 7, 2013]. Retrieved from the Internet: <URL: http://www.pccnaturalmarkets.com/sc/0506/sc0506-repellents.html>.*
(W1) "Natural-Homeremedies-For-Life". Internet Archive Date: Sep. 29, 2009[Retrieved from the Internet on: Nov. 22, 2014]. Retrieved from the Internet on: <URL: https://web.archive.org/web/20090929230252/http://www.natural-homeremedies-for-life.com/natural-mosquito-repellent.html>.*
(X1) "Garden mentors". Web Date: Jun. 18, 2008 [Retrieved from the internet on: Nov. 22, 2014]. Retrieved from the Internet: <URL: https://web.archive.org/web/20090929230252/http://www.natural-homeremedies-for-life.com/natural-mosquito-repellent.html>.*
(U1) Tipnut.com. Internet Archive Date: Apr. 18, 2009 [Retrieved from the Internet on: Nov. 22, 2014]. Retrieved from: <URL: https://web.archive.org/web/20090418063954/http://tipnut.com//>.*
"p-Menthane-3, 8-diol" from Wikipedia http://en.wikipedia.org/wiki/p-Menthane-3,8-diol (1 of 1) [Retrieved from the Internet on Sep. 29, 2011].
"100% P.E.O." 100% Pure Essential Oils "Lemon Eucalypus Oil" www.100pureessentialoils.com/lemon-eucalyptus-oil.html (1 of 1) [Retrieved from the Internet on Sep. 29, 2011].
"100% P.E.O." 100% Pure Essential Oils "Lemongrass Oil" www.100pureessentialoils.com/lemongrass-oil.html (1 of 1) [Retrieved from the Internet on Sep. 29, 2011].
New Directions Aromatics "Litsea Cubeba" www.newdirectionsaromatics.com/litsea-cubeba-essential-oil (3 pages) [Retrieved from the Internet on Sep. 29, 2011].
"100% P.E.O." 100% Pure Essential Oils "*Geranium* (Bourbon) Oil" www.100pureessentialoils.com/geranium-bourbon-oil.html (3 pages) [Retrieved from the Internet on Sep. 29, 2011].
Mission Essentials website www.mission-essentials.com [Retrieved from the Internet on Sep. 30, 2011].

* cited by examiner

Primary Examiner — Amy L Clark
(74) Attorney, Agent, or Firm — B. Craig Killough; Barnwell Whaley Patterson Helms

(57) ABSTRACT

An alcohol-free insect repellent composition includes an essential oil mixture that includes: (a) from about 30 to about 60 weight % of lemongrass oil; (b) from about 15 to about 40 weight % of essential oil of lemon eucalyptus; (c) from about 10 to about 30 weight % of rose geranium oil; and (d) from about 2 to about 20 weight % of *Litsea cubeba* oil; the balance of the insect repellent composition to 100 weight % being water; wherein the insect repellent composition further comprises a weight ratio of lemongrass oil to lemon eucalyptus oil of between about 1:10 and about 10:1; a weight ratio of lemongrass oil to *Litsea cubeba* oil of between about 6:1 and about 1:1; a weight ratio of rose geranium oil to *Litsea cubeba* oil of between about 5:1 and about 1:5; and a weight ratio of rose geranium oil to lemon eucalyptus oil of between about 5:1 and about 1:5.

20 Claims, No Drawings

NATURAL INSECT REPELLENT COMPOSITIONS

BACKGROUND OF THE INVENTION

1. Technical Field

The present invention relates to an insect repellent composition, more particularly a liquid composition suitable for application to human skin for repelling mosquitoes and other insects.

2. Background Information

The most numerous and successful animals on earth are undoubtedly insects. Despite some helpful species, a great many insects are a bane to humans, no more so than in the hot, humid South. Many months of the year, people venturing outdoors are plagued by biting insects, such as mosquitoes, gnats, noseeums (biting midges), flies, ticks, head lice, fire ants, fleas, and other insects. Of course, bites and stings inflicted by "biting" insects are often itchy and can become infected. Aside from the annoyance of being surrounded by swarming insects in the air or on the ground (e.g., gnats, noseeums flies, fleas, ants, cockroaches), many biting/stinging insects such as fleas, mosquitoes, and flies, are vectors for serious diseases, such as malaria, Rocky Mountain Spotted Fever, Lyme disease, leishmaniasis, dengue fever, and West Nile fever. Scientists have developed one effective insecticide after another over the years, only to discover later on that their compounds cause harm to humans and animals and/or the environment (e.g., DEET—N, N-diethyl-m-toluamide). The quandary many parents face is whether to keep themselves and their children indoors during the months that mosquitoes and other insects are a problem, or risk applying a possibly harmful insect repellent to the child's skin so they can venture outside.

Products claiming to be safe for the environment have risen in popularity in the last few decades. Unfortunately, the words "natural insect repellent" are associated in the minds of many with ineffectiveness and an unpleasant, pungent smell. Most adults and children object to wearing a bad-smelling, sticky insect repellent formula on their skin, even if it does repel insects.

The US Food & Drug Administration (FDA) has a "Generally Regarded As Safe" (GRAS) classification for certain compounds. The compositions of the present invention include GRAS-classified essential oils, have a pleasant odor, and have been proven effective in repelling insects. Although GRAS-classified essential oils of the present formulas have been used separately as insect repellents in the past, they have not heretofore been combined with the select ingredients of the present formulations in order to achieve an over-all surprisingly pleasant-smelling and effective insect repellent.

BRIEF SUMMARY OF THE INVENTION

The present invention is an alcohol-free insect repelling composition, comprising: (a) from about 30 to about 60 weight % of lemongrass oil; (b) from about 15 to about 40 weight % of essential oil of lemon eucalyptus; (c) from about 10 to about 30 weight % of rose geranium oil; and (d) from about 2 to about 20 weight % of *Litsea cubeba* oil; the balance of the insect repellent composition to 100 weight % being water; wherein the insect repellent composition is free of non-naturally occurring, or chemical, ingredients.

Advantages of the insect repelling composition of the present invention include the following: 1) contains essential oils that are formulated in water without any harmful, drying alcohols, chemical fragrances, or chemical preservatives added; 2) is effective in repelling insects; 3) does not feel like a sticky coating when sprayed onto human skin, yet is relatively long lasting; 4) is a natural insect repellent, yet it smells good and is not objectionable to children; 5) is environmentally safe and can also safely be used on dogs and horses; and 6) can easily be applied to human skin with no known adverse effects.

DETAILED DESCRIPTION OF THE INVENTION

In the following description, like reference characters designate like or corresponding parts throughout the several views.

The present formula comprises: lemongrass oil, rose geranium oil, lemon eucalyptus oil, and *Litsea cubeba* oil, which can be mixed into the formula in any order. All of the essential oils act together as the active insect repellent component of the present composition.

The insect repelling composition of the present invention may be topically applied and used in manufacturing products with insect repellent capability. The present formula is preferably poured into spray bottles, each with a fine spray nozzle. Rather than soaking the skin, preferably a fine spray mist is sprayed onto the user's skin. The present composition is preferably shaken just prior to each use. The formulations of the present invention are believed to be effective in repelling mosquitoes, gnats, noseeums (biting midges), flies, ticks, head lice, fire ants, cockroaches, and fleas, among other insects, from the coated area. The present formula is also effective in repelling insects from dogs and horses. Each essential oil in the present formula is carefully selected after experimentation in order to attain a certain objective. The overall objective was to arrive at a formula that will repel insects yet is safe for the skin of children and adults and will not damage the environment short term or long term. Before using the present composition on a young or sensitive subject, it may be desirable to test the spray composition of the present invention on a patch of the intended subject's skin. Percentages by weight of the components of the essential oil mixture for a preferred insect repellent composition herein are as follows, followed by the more preferred levels and then the most preferred level for that component:

Lemongrass: about 30-60% of the essential oil mix, more preferably about 45-55%, most preferably about 47-50%;

Lemon Eucalyptus: about 15-40% of the essential oil mix, more preferably about 20-30%, most preferably about 25-27%;

Rose Geranium: about 10-30% of the essential oil mix, more preferably about 15-20%, most preferably about 15-18%;

Litsea Cubeba: about 2-20% of the essential oil mix, more preferably about 5-15%, most preferably about 8-10%.

The compositions of the present invention include Lemongrass oil, which is made from distilled leaves of *Cymbopogon citratus*. Lemongrass oil has a strong smell and is used in aromatherapy as a cellulite remedy and to calm the nerves. It is said to be useful for treating oily skin and hair, and as a fly, flea, and tick repellent. Lemongrass oil is said to have an antiseptic effect and an antibacterial effect, and therefore to be helpful in fighting infections.

Secondly, the compositions of the present invention include essential oil of the lemon eucalyptus, *Corymbia citriodora*, and its active compound p-menthane-3,8-diol (PMD). P-menthane-3,8-diol, also called menthoglycol, is made from acid modifying the oil of the Latin American plant *Corymbia citriodora*.

Lemon eucalyptus oil is said to be as effective as DEET (N, N-diethyl-m-toluamide) in insect repellents, and is believed to be approved by the Center for Disease Control (CDC) and the Food and Drug Administration (FDA) for use against the mosquitoes known to carry West Nile virus, which causes West Nile fever. Oil of lemon eucalyptus is reddish in color and is said to have a menthol-like smell and a coolant-like effect. It is apparently used in aromatherapy for relief of congestion, emphysema, and smokers' cough, as well as for sore throats. It is said to be an antifungal and anti-infectious agent suitable for helping against respiratory and skin infections, and to have antinflammatory and insecticidal properties. It can apparently be applied by inhalation, bath, lotion, ointment, diffuser, or a room spray. According to contraindications, lemon eucalyptus oil should be diluted prior to applying it on the skin.

Thirdly, the compositions of the present invention also include rose geranium oil from *Pelargonium graverlens*. The main ingredient of rose geranium oil is gerinol, which is said to be an insect repellent for repelling mosquitoes, certain kinds of flies, cockroaches, fire ants, fleas, gnats, dog ticks, lone star ticks, and noseeums. Rose geranium is also said to help clear acne, fade scars and spots on the skin, exfoliate skin, and control oily skin, and to help those with shingles, eczema, and itchy dry skin. It is said to have no known toxicity, although it can apparently cause irritation if used directly on the skin, and to be GRAS (Generally Regarded as Safe) and approved by the FDA.

Fourthly, the formulations herein include the uncommonly used oil of *Litsea cubeba*. *Litsea cubeba* is apparently a small tropical plant originally from China. The thin, transparent, yellow essential oil is said to be extracted by steam distillation from its small, pepper-like fruits. This essential oil is said to have calming and anti-inflammatory effects. It is said to have astringent, antiseptic, hypotensive, stimulant, and insecticidal effects.

*Litsea cubeba* enhances the pleasant smell of the insect repellent compositions of the present invention, and, surprisingly, is believed to help the composition ingredients blend together, and to increase the effective life of the repellent compositions of the present invention. *Litsea cubeba* is believed to function as a preservative in the present formulations, and to function synergistically with other ingredients of the present formulas.

The active ingredients in the insect repellent composition herein preferably total between about 10 weight % and about 60 weight % of the finished product, preferably between about 15 weight % and about 30 weight %, most preferably between about 20 weight % and about 25 weight % of active ingredient. The essential oils are the active ingredient. This contrasts with most commonly available chemical insect repellents compositions, which average between about 2 and about 10 weight % of active ingredients. The composition of the present invention is preferably a sprayable liquid, although it could less preferably be in the form of a gel or foam. The repellent composition of the present invention is preferably sprayed on human skin, although it can also be sprayed on the coats, fur, or skin of dogs and horses, on clothing, or on textiles indoors in offices and homes to repel insets and to impart a pleasant smell. The present composition can be sprayed on or combed through the hair of human beings, or dogs and horses, to eliminate insects that can live in the hair, such as lice and fleas. Alternatively, wipes can be soaked overnight in the present composition and used to wipe exposed skin prior to going outdoors.

The weight ratio of lemongrass oil to lemon eucalyptus oil in the insect repellent composition herein varies from about 1:10 to about 10:1, more preferably about 1:5 and about 5:1, most preferably between about 1:2 and about 2:1.

The weight ratio of lemongrass oil to rose geranium oil in the insect repellent composition herein varies from between about 6:1 and about 1:1, most preferably between about 4:1 and about 2:1.

The weight ratio of lemongrass oil to *Litsea cubeba* oil in the repellent composition herein varies from between about 6:1 and about 1:1, most preferably between about 5:1 and about 2:1.

The weight ratio of rose geranium oil to *Litsea cubeba* oil in the insect repellent composition herein varies from between about 5:1 and about 1:5, most preferably between about 2:1 and about 1:2.

The weight ratio of rose geranium oil to lemon eucalyptus oil in the insect repellent composition herein varies from between about 5:1 and about 1:5, most preferably between about 2:1 and about 1:2.

All four of the essential oils described herein and no others have been found to work optimally in repelling insects, yet with a pleasing scent and soft feel on the skin. A more preferred weight ratio in the essential oil mixture of the present insect repellent composition is 6 parts lemongrass oil to 2 parts rose geranium oil to 1 part *Litsea cubeba* oil to 3 parts lemon eucalyptus oil (6 L:2 RG:1 LC:3 LE).

The balance of the insect repellent composition is water, preferably distilled and/or deionized water. The weight ratio of essential oils to water in the insect repellent composition herein varies from between about 1:20 and about 1:2, most preferably between about 1:5 and about 1:4. The present composition, then, is an aqueous formulation.

The essential oils are blended in a suitably sized container in the proportions outlined herein. The essential oil mixture is then mixed with the distilled water. Other desired ingredients, if any, are added. The formula is shaken by hand or mechanically stirred or shaken. About one quart of essential oil mixture is mixed with 1 gallon of distilled water, resulting in a 20 weight % total essential oil solution. The desired amount of insect repellent solution is then poured into each spray bottle.

As used herein, an "insect repellent composition" is a formula that repels insects or other pest arthropods and that can be applied to skin or another surface.

As used herein, an "essential oil" is any concentrated, hydrophobic liquid with volatile aroma compounds from plants. Suitable essential oils for use herein include, but are not limited to, an essential oil selected from lemongrass oil, rose geranium oil, oil of lemon eucalyptus, and *Litsea cubeba* oil. Many essential oils are extracted from their respective plants by steam distillation, cold pressing, or CO2 extraction.

By "alcohol free" herein is meant substantially free of any alcohols; for example, the insect repellent composition herein is free of the ethyl alcohol that is used in many conventional insect repellent formulas. (It is possible that trace amounts may be present in the present composition, or that a plant derived alcohol component could be incorporated into the composition, but no alcohol is added.)

By "non-naturally occurring ingredients" herein is meant ingredients, or components, that do not occur in nature. The present composition is free, then, of any artificial, or chemical, ingredients.

The insect repellent compositions of the present invention preferably do not include the following: 1) other active insecticidal ingredients, such as DEET (N,N-diethyl-m-toluamide) or oil of citronella; 2) other carriers such as petroleum jelly, mineral oil, baby oil, paraffin oil, or vegetable oil, or alcohols or other compounds known to cause skin to dry out; 3) chemical fragrances, like those used in the past in insect repellents, such as musk, sandalwood, and patchouly, or conventional fragrance enhancers; or 4) surfactants, such as sodium lauryl sulfate, ammonium lauryl sulfate, sodium laureth sulfate, and polysorbate 80. These ingredients are not needed for the present compositions to perform effectively. Thus, the insect repellent formulas herein do not include ethanol, isopropyl alcohol, propanol, octanol, or any other alcohols, or vinegar. They do not include any witch hazel, cedar oils, chemical preservatives, or any unnatural or harmful chemicals.

The insect repelling compositions herein preferably do not include abrasives, chelating agents, thixotropic agents, antioxidants, emollients, sunscreen agents, formula thickeners such as propylene glycol or glycerin, or chemical preservatives such as parabens, skincare agents such as lanolin or skin cleansers, or pH adjusting agents. The insect repellent compositions herein need not include emulsifiers for stabilizing the active component oils in solution, such as surfactants, alkyl polyoxyethylene ether esters, ethoxylated or nonethoxylated sorbitan monooleate, polyglycerin fatty acid esters, fatty alcohol and sodium stearoyl lactylate, or soybean oil.

The compositions of the present invention may include certain vitamins, such as B1, B6, B12, C, D, and E for skin health, but not vitamin A. The compositions of the present invention may also include the juice of aloe vera for additional skin protection.

This insect repellent composition has a pleasant feel once it has been sprayed or rubbed on skin, too. It is not sticky and has a pleasant smell. Children tolerate it well. Compositions of the present invention are reported to have a calming, soothing effect on the skin, much like the effect of aroma therapy.

Without meaning to be bound by theory, it is believed that the compositions of the present invention have a topical antiseptic effect and an antibacterial effect, and are therefore helpful in treating infected bug bites and other slight skin infections. The present compositions are anecdotally reported to relieve itching from, for example, previous red ant bites. They are also believed to have an anti-inflammatory effect.

To make a formula according to the present invention, the four essential oil ingredients of the present composition, lemongrass oil, rose geranium oil, lemon eucalyptus oil, and *Litsea cubeba* oil, can be added to and mixed with the water, in any order. The mixing vessels are at room temperature. No heat is applied to the mixing vessels, nor is the pressure or humidity inside the mixing vessels controlled. The mixing vessels can be open, though they are preferably covered to prevent dust, etc. from entering. Once it has been mixed for about five minutes, the insect repellent composition is ready to pour into individual containers for sale, such as 0.5-16 ounce spray bottles, and use. Each individual spray bottle should be shaken lightly before each application of the insect repellent composition.

A preferred method for preparing an insect repellent composition according to the present invention is as follows. The desired amount of distilled water is placed in a mixing vessel, such as a five gallon stainless steel container. The appropriate amounts of the four essential oils, lemongrass oil, rose geranium oil, lemon eucalyptus oil, and *Litsea cubeba* oil, are mixed together at room temperature in any order in a one or two gallon container using a conventional mechanical stirrer for between about two and twenty minutes. A mechanical stirrer or other mixing device positioned at about the center of the five gallon mixing vessel is turned on a low speed, and the essential oil mixture is poured into the five gallon mixing vessel, stirring for between about two and five minutes. Levels are checked and a small amount of water is then added if needed to bring the mixture to 100%. There is no need to add emulsifiers or to measure or adjust the pH of the resultant composition. There is no need to allow the formulation to rest before proceeding to the next step, pouring it into bottles.

An alternate method for preparing an insect repellent composition according to the present invention is as follows. The four essential oils as described herein are mixed with distilled water in a container with a natural preservative added, such as polysorbate 80 (a nonionic surfactant and emulsifier). The resulting solution is then mixed and heated for a few minutes (e.g. five minutes), followed by cooling the mixture for a few minutes (e.g., ten minutes) back to ambient temperature. The same method may alternatively be used for a solution according to the present invention containing the same four essential oils, distilled water, and a small amount of a natural, non-alcohol-containing preservative. The latter ingredient is believed to help stabilize the present composition.

As would be recognized by one skilled in the art, the compositions of the present invention can be made by any suitable conventional method in which the four essential oils described herein are combined to create a formula that is suitable for application to the surface of human skin, or the coats of dogs and horses, or any surface where the repelling of insects is advantageous. Many people do not like to apply bug sprays to the face in particular, especially a child's face, because of safety concerns. The present compositions can safely be applied to the face and hair.

The present invention contemplates other means of distributing the present insect repellent composition over human skin, on articles of clothing, or on a pet, in addition to spraying it on. Any applicator suitable for distributing the present composition may be used. For example, an applicator stick or wipes soaked in the present composition may be employed. The present composition may alternatively be incorporated into a candle. When the candle wick is lit, the composition slowly volatilizes into the surrounding air.

A preferred spray-on insect repellent composition herein, comprises: (a) from about 8% to about 12% by volume of lemongrass oil; (b) from about 3% to about 7% by volume of lemon eucalyptus oil; (c) from about 1% to about 6% by volume of rose geranium oil; and (d) from about 1% to about 5% by volume of *Litsea cubeba* oil; the balance of the insect repellent composition to 100 weight % being distilled water; the insect repellent composition being substantially free of alcohol.

EXAMPLES

The following examples illustrate the invention without limitation. Unless otherwise described, percentages constitute proportion by weight of the total composition.

Example 1

A formulation representing a preferred embodiment of the present invention is formulated using the ingredients listed below in the specified amounts. The four essential oils listed below are blended in a five gallon container at room temperature using a mechanical stirrer set at low speed. The essential oil mixture is then poured into the specified amount of distilled water, which is held in a second, five gallon mixing vessel at room temperature. The mixture is stirred for about five minutes using a mechanical stirrer set at low speed.

Example 1

Essential Oil Mixture and Amounts 48 weight % of lemongrass oil;

26 weight % of rose geranium oil;

17 weight % of lemon eucalyptus oil; and 9 weight % of *Litsea cubeba* oil.

One quart of the essential oil mixture is mixed with one gallon of distilled water, resulting in a 20% total essential oil solution. The resulting insect repellent solution is poured into spray bottles. It provides excellent protection against insects landing on and stinging the skin when the subject's skin is sprayed thoroughly every two to four hours, depending upon the environment and the individual's tolerance of insects.

Example 2

After shaking a spray bottle containing the composition of Example 1, a few pumps of the composition of Example 1 are sprayed onto a person's exposed forearms. The subject then enters an area where black flies are congregated around full garbage cans. In the presence of the treated forearms, the flies immediately fly away and do not return to the garbage can area until the treated subject exits the area.

In a separate instance, the same subject with untreated forearms enters the same area. The untreated arms exhibit no repellency effect; the flies continue buzzing around the garbage cans and the subject.

After the test, the composition of Example 1 is sprayed around the garbage can area. Flies are observed to scatter from the sprayed area and not return for several hours.

Example 3

The composition of Example 1 is sprayed on each of the subject's forearms. The subject then goes outdoors and golfs on a golf course for 120 minutes. Although many mosquitoes are seen in the air, no mosquitoes are observed landing on either of the subject player's forearms. The subject reports no insect bites on the sprayed skin areas on either forearm. The subject does report insect bites on other, untreated, exposed parts of his body. 200 subjects are tested in this manner with the same results. The Example 1 bug spray appears to repel mosquitoes. No irritations or other negative reactions are reported by the players.

Example 4

About one ounce of the composition of Example 1 is mixed in with about one pound of warmed, liquefied candle wax. A pillar candle with a wick is formed and allowed to cool and harden.

Example 5

The four essential oil ingredients of the present composition listed below are added to and mixed with the distilled water in the order shown in a five gallon container at room temperature. No heat is applied to the container, nor is the pressure or humidity controlled.

Example 5

Ingredients and Amounts 10 weight % of lemongrass oil;

3 weight % of rose geranium oil;

5 weight % of lemon eucalyptus oil;

2 weight % of *Litsea cubeba* oil; and 80 weight % of distilled water; total 100 weight %.

Once it has been stirred or shaken for about five minutes, the insect repellent composition of Example 5 is poured into individual 4 ounce spray bottles. Each individual spray bottle is lightly shaken before each application of the insect repellent composition.

Example 6

An alternate formulation of the present invention contains the ingredients listed below in the amounts specified. The first four ingredients listed below are blended in a five gallon container using a mechanical stirrer set at low speed. This essential oil mixture is then poured into the specified amount of distilled water, which is held in a second five gallon mixing vessel at room temperature. The juice squeezed by hand from an aloe vera plant is then added and stirred in. One quart of the essential oil mixture is mixed with one gallon of distilled water, resulting in a 20% total essential oil solution. The mixture is stirred for about twenty minutes using a mechanical stirrer set at low speed.

Example 6

Ingredients and Amounts 10 weight % of lemongrass oil;

3 weight % of rose geranium oil;

5 weight % of lemon eucalyptus oil;

2 weight % of *Litsea cubeba* oil;

about 1 weight % of aloe vera juice; and 80 weight % of distilled water; total 100 weight %.

Once it has been stirred or shaken for about five minutes, the insect repellent composition of Example 6 is poured into individual 4 ounce spray bottles. The individual spray bottle is lightly shaken before each application of the insect repellent composition.

Example 7

An alternate formulation of the present invention contains the ingredients listed below in the amounts specified. The first four ingredients listed below are blended in a five gallon container using a mechanical stirrer set at low speed. The essential oil mixture is then poured into the specified amount of distilled water, which is held in a second five gallon mixing vessel at room temperature. One quart of the essential oil mixture is mixed with one gallon of distilled water, resulting in a 20% total essential oil solution. The mixture is stirred for about ten minutes using a mechanical stirrer set at medium speed.

Example 7

Ingredients and Amounts 10 weight % of lemongrass oil;
3 weight % of rose geranium oil;
5 weight % of lemon eucalyptus oil;
2 weight % of *Litsea cubeba* oil;
about 1 weight % of vitamin E oil; and
80 weight % of distilled water; total 100 weight %.

The composition is poured into a pump bottle, shaken lightly, and sprayed on the subject's forearms. In a separate instance, disposable cotton gauze pads pre-soaked in the composition of Example 7 for about 24 hours are used to wipe the subject's forearms prior to the subject's outdoor exposure to mosquitoes and gnats. Mosquitoes and gnats do not closely approach or light on the sprayed skin area, or the wiped skin area in the separate instance. After outdoor exposure to the insects, the subject has not received mosquito bites on the coated skin area, regardless of whether the forearms were sprayed or wiped.

Example 8

Several ounces of the composition of Example 5 are placed in a small cup. Four active adult head lice picked from a child's hair appear to die immediately upon being placed in the liquid. The composition of Example 5 is poured on a hair comb and the comb is combed through the subject child's hair. After combing, several dead adult head lice are observed in the comb. Afterward, the composition of Example 5 is misted over the hair and on the child's pillow and bedding.

Example 9

Exposed skin of multiple children is sprayed with the composition of Example 5 after shaking the spray bottle. Parents of smaller subject children, ages 3-5 years, apply the spray by spraying it on their hands and then applying it to the children's faces. Parents report that the subject children like the smell of the composition, though they normally do not tolerate other bug sprays. The children do not report burning or any other complaints associated with the spray. Before and after application of the composition, the subjects play in an outdoor environment where many flying mosquitoes and noseeums are observed. All of the subjects report immediate relief from close flying insects and bug bites when comparing before and after treatment with the composition of the present invention.

Example 10

Exposed skin of multiple subjects is sprayed with the composition of Example 5. The subjects then go outdoors for several hours in areas where red ant hills are seen. No new red ant bites are reported. Subjects also report that the bug spray composition is soothing, calming, and relieved itching from previous red ant bites in the sprayed areas of the skin.

From the foregoing it can be realized that the described formulas of the present invention may be easily and conveniently utilized for repelling insects. It is to be understood that any dimensions given herein are illustrative, and are not meant to be limiting.

While preferred embodiments of the invention have been described using specific terms, this description is for illustrative purposes only. It will be apparent to those of ordinary skill in the art that various modifications, substitutions, omissions, and changes may be made without departing from the spirit or scope of the invention, and that such are intended to be within the scope of the present invention as defined by the following claims. It is intended that the doctrine of equivalents be relied upon to determine the fair scope of these claims in connection with any other person's product which fall outside the literal wording of these claims, but which in reality do not materially depart from this invention. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is:

1. An alcohol-free insect repellent composition comprising:
   (a) from about 45 to about 55 weight % of lemongrass oil;
   (b) from about 20 to about 30 weight % of essential oil of lemon eucalyptus;
   (c) from about 15 to about 20 weight % of rose geranium oil; and
   (d) from about 2 to about 15 weight % of *Litsea cubeba* oil; the balance of the insect repellent composition to 100 weight % being water; wherein the insect repellent composition further comprises a weight ratio of lemongrass oil to lemon eucalyptus oil of between about 1:10 and about 10:1; a weight ratio of lemongrass oil to *Litsea cubeba* oil of between about 6:1 and about 1:1; and a weight ratio of rose geranium oil to *Litsea cubeba* oil of between about 5:1 and about 1:5.

2. The insect repellent composition of claim 1, wherein the insect repellent composition mixture comprises from about 5 to about 10 weight % of the *Litsea cubeba* oil.

3. The insect repellent composition of claim 1, wherein the insect repellent composition further comprises a weight ratio of lemongrass oil to rose geranium oil of between about 6:1 and about 1:1; and a weight ratio of rose geranium oil to lemon eucalyptus oil of between about 5:1 and about 1:5.

4. The insect repellent composition of claim 1, wherein the insect repellant composition repels mosquitoes and gnats.

5. The insect repellent composition of claim 1, wherein the insect repellent composition is a spray-on composition for application to human skin.

6. The insect repellent composition of claim 1, wherein the insect repellent composition is applied to skin, fur, or coat of a dog or horse.

7. The insect repellent composition of claim 1, wherein the insect repellent composition repels fleas or midges.

8. The insect repellent composition of claim 1, wherein the insect repellent does not comprise other active, insecticidal ingredients; and the weight ratio of lemongrass oil to lemon eucalyptus oil is between about 1:5 and about 5:1', the weight ratio of lemongrass oil to rose geranium oil is between about 4:1 and about 2:1; the weight rat of lemongrass oil to *Litsea cubeba* oil is between about 6:1 and about 2:1; the weight ratio of rose geranium oil to *Litsea cubeba* oil is between about 2:1 and about 1:2; and the weight ratio of rose geranium oil to lemon eucalyptus oil is between about 2:1 and about 1:2.

9. The insect repellent composition of claim 1, wherein the lemongrass oil to lemon eucalyptus oil to rose geranium oil to *Litsea cubeba* oil weight ratio is 6 parts of the lemongrass oil to 3 parts lemon eucalyptus oil to 2 parts of the rose geranium oil to 1 part of the *Litsea cubeba* oil.

10. The insect repellent composition of claim 1, wherein the insect repellent composition is substantially free of a pH adjusting agent, and is substantially free of artificial preservatives.

11. The insect repellent composition of claim 1, wherein the insect repellent composition is substantially free of chemical fragrances.

12. The insect repellent composition of claim 1, wherein the insect repellent composition is soaked into a wipe for application to human skin.

13. The insect repellent composition of claim 1, further comprising from about 0.2 to about 2 weight % of vitamin E.

14. The insect repellent composition of claim 1, further comprising from about 0.2 to about 2 weight % of aloe vera juice.

15. A spray-on insect repellent composition, comprising:
 (a) from about 8% to about 12% by volume of lemongrass oil;
 (b) from about 3% to about 7% by volume of lemon eucalyptus oil;
 (c) from about 1% to about 6% by volume of rose geranium oil; and
 (d) from about 1% to about 5% by volume of *Litsea cubeba* oil; the balance of the insect repellent composition to 100 weight % being water; the insect repellent composition being substantially free of alcohol; and wherein the insect repellent composition further comprises a weight ratio of lemongrass oil to lemon eucalyptus oil of between about 1:10 and about 10:1; a weight ratio of lemongrass oil to *Litsea cubeba* oil of between about 6:1 and about 1:1; a weight ratio of rose geranium oil to *Litsea cubeba* oil of between about 5:1 and about 1:5; and a weight ratio of rose geranium oil to lemon eucalyptus oil of between about 5:1 and about 1:5.

16. The insect repellent composition of claim 15, wherein the insect repellent composition does not comprise any additional carriers.

17. The insect repellent composition of claim 15, wherein the insect repellent composition is substantially free of any chemical fragrances.

18. The insect repellent composition of claim 15, wherein the lemongrass oil to lemon eucalyptus oil to rose geranium oil to *Litsea cubeba* oil weight ratio is 6 parts lemongrass oil to 3 parts lemon eucalyptus oil to 2 parts of the rose geranium oil to 1 part *Litsea cubeba* oil.

19. The insect repellent composition of claim 15, wherein the insect repellent composition is a spray-on composition for application to human skin; and the weight ratio of lemongrass oil to lemon eucalyptus oil is between about 1:5 and about 5:1; the weight ratio of lemongrass oil to rose geranium oil is between about 4:1 and about 2:1; the weight ratio of lemongrass oil to *Litsea cubeba* oil is between about 6:1 and about 2:1; the weight ratio of rose geranium oil to *Litsea cubeba* oil is between about 2:1 and about 1:2; and the weight ratio of rose geranium oil to lemon eucalyptus oil is between about 2:1 and about 1:2.

20. An alcohol-free composition for repelling insects, the insect repellent composition comprising an essential oil mixture, the essential oil mixture consisting essentially of:
 (a) from about 30 to about 60 weight % of lemongrass oil;
 (b) from about 15 to about 40 weight % of essential oil of lemon eucalyptus;
 (c) from about 10 to about 30 weight % of rose geranium oil; and
 (d) from about 2 to about 20 weight % of *Litsea cubeba* oil; the balance of the insect repellent composition to 100 weight % being water; wherein the insect repellent composition further comprises a weight ratio of lemongrass oil to lemon eucalyptus oil of between about 1:10 and about 10:1; a weight ratio of lemongrass oil to *Litsea cubeba* oil of between about 6:1 and about 1:1; and a weight ratio of rose geranium oil to *Litsea cubeba* oil of between about 5:1 and about 1:5.

* * * * *